(12) United States Patent
Han et al.

(10) Patent No.: US 10,952,642 B2
(45) Date of Patent: Mar. 23, 2021

(54) STRAIN SENSOR UNIT AND SKIN SENSOR MODULE COMPRISING THE SAME

(71) Applicants: AMOREPACIFIC CORPORATION, Seoul (KR); MASSACHUSETTS INSTITUTE OF TECHNOLOGY, Cambridge, MA (US)

(72) Inventors: Jiyeon Han, Yongin-si (KR); Han-Wool Yeon, Cambridge, MA (US); Eunjoo Kim, Yongin-si (KR); Jeehwan Kim, Cambridge, MA (US); Kyusang Lee, Charlottesville, VA (US); Haekwang Lee, Yongin-si (KR)

(73) Assignees: AMOREPACIFIC CORPORATION, Seoul (KR); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 617 days.

(21) Appl. No.: 15/808,416

(22) Filed: Nov. 9, 2017

(65) Prior Publication Data

US 2019/0133491 A1    May 9, 2019

(51) Int. Cl.
*A61B 5/00*    (2006.01)
*A61B 5/103*    (2006.01)
(Continued)

(52) U.S. Cl.
CPC ............ *A61B 5/103* (2013.01); *A61B 5/6814* (2013.01); *A61B 5/6824* (2013.01); *H01L 27/20* (2013.01);
(Continued)

(58) Field of Classification Search
CPC ..... A61B 5/103; A61B 5/6814; A61B 5/6824; H01L 41/9475; H01L 41/053;
(Continued)

(56) References Cited

U.S. PATENT DOCUMENTS 5,335,210 A * 8/1994 Bernstein ............... G01H 11/06
367/163
6,475,823 B1 * 11/2002 Sakano .................... H03H 3/02
257/419

(Continued)

FOREIGN PATENT DOCUMENTS

KR    101746492    6/2017

OTHER PUBLICATIONS

Jeehwan Kim, et al., "Principle of direct van der Waals epitaxy of single-crystalline films on epitaxial graphene", Nature Communications, (2014), pp. 1-7.

(Continued)

*Primary Examiner* — Sean P Dougherty
(74) *Attorney, Agent, or Firm* — Cantor Colburn LLP

(57) ABSTRACT

A strain sensor unit and a skin sensor module comprising the same are provided. The strain sensor unit according to an embodiment of the present disclosure includes a substrate having a through-hole, and including a first electrode and a second electrode formed at one side and the other side of the through-hole on one surface of the substrate, a piezoelectric device drawn from the first electrode and extending inward the through-hole, and a piezoresistor drawn from the second electrode and extending inward the through-hole, wherein the piezoresistor overlaps with a whole or part of the piezoelectric device.

8 Claims, 12 Drawing Sheets

(51) Int. Cl.
  *H01L 27/20* (2006.01)
  *H01L 41/08* (2006.01)
  *H01L 41/047* (2006.01)
  *H01L 41/053* (2006.01)
  *H01L 41/113* (2006.01)
  *H01L 41/312* (2013.01)

(52) U.S. Cl.
  CPC ........ *H01L 41/0475* (2013.01); *H01L 41/053* (2013.01); *H01L 41/081* (2013.01); *H01L 41/1132* (2013.01); *H01L 41/312* (2013.01); *A61B 2562/0261* (2013.01)

(58) Field of Classification Search
  CPC ... H01L 41/081; H01L 41/1132; H01L 41/41; H01L 41/312
  See application file for complete search history.

(56) References Cited

U.S. PATENT DOCUMENTS

| | | | | |
|---|---|---|---|---|
| 7,943,413 | B2* | 5/2011 | Kasai | H04R 19/005 257/416 |
| 8,209,023 | B2* | 6/2012 | Zhou | A61N 1/0543 607/115 |
| 9,927,311 | B2* | 3/2018 | Kang | G01H 11/06 |
| 10,143,081 | B2* | 11/2018 | Wang | C08L 53/02 |
| 2003/0107456 | A1* | 6/2003 | Nishihara | H03H 3/02 333/187 |
| 2005/0218398 | A1* | 10/2005 | Tran | B82Y 10/00 257/14 |
| 2006/0183990 | A1* | 8/2006 | Tolvanen | A61B 5/6805 600/386 |
| 2007/0261910 | A1* | 11/2007 | Kasai | G01H 11/06 181/142 |
| 2008/0007139 | A1* | 1/2008 | Kawamura | H03H 9/02228 310/313 B |
| 2010/0064804 | A1* | 3/2010 | Kawakubo | G01C 19/56 73/504.03 |
| 2011/0319787 | A1* | 12/2011 | Lamoise | A61B 5/103 600/549 |
| 2013/0133435 | A1* | 5/2013 | Muramatsu | G01B 1/00 73/799 |
| 2013/0234558 | A1* | 9/2013 | Tsuda | H01L 41/0477 310/313 B |
| 2015/0035411 | A1* | 2/2015 | Kawamura | G01L 1/16 310/330 |
| 2016/0111628 | A1* | 4/2016 | Yonemura | H01L 41/29 310/365 |
| 2016/0123820 | A1* | 5/2016 | Kang | G01H 11/06 324/693 |
| 2017/0131168 | A1* | 5/2017 | Shimoyama | G01L 9/0042 |
| 2017/0323908 | A1* | 11/2017 | Yamazaki | H01L 27/1225 |

OTHER PUBLICATIONS

Kyung-In Jang, et al., "Self-assembled three dimensional network designs for soft electronics", Nature Communications, (2017), pp. 1-10.

Ming Liang Jin, et al., "An Ultrasensitive, Visco-Poroelastic Artificial Mechanotransducer Skin Inspired by Piezo2 Protein in Mammalian Merkel Cells", Adv. Mater., (2017), vol. 29, pp. 1-9.

Ming Liang Jin, et al., "An Ultrasensitive, Visco-Poroelastic Artificial Mechanotransducer Skin Inspired by Piezo2 Protein in Mammalian Merkel Cells", Advance Materials, (2017), pp. 1-34.

Y. Huang, et al., "Experimental study and modeling of the influence of screw dislocations on the performance of AuÔn-GaN Schottky diodes", Journal of Applied Physics, Nov. 1, 2013, vol. 9, No. 9, pp. 5771-5775.

Yunjo Kim, et al., "Remote epitaxy through graphene enables two-dimensional material-based layer transfer", Nature, Apr. 20, 2017, vol. 544, pp. 340-343.

* cited by examiner

STRAIN SENSOR UNIT AND SKIN SENSOR MODULE COMPRISING THE SAME

BACKGROUND

1. Field

The present disclosure relates to a strain sensor unit that is worn on the skin to monitor physiological skin motions in real time and a skin sensor module comprising the same, and more particularly, to a strain sensor unit that allows for interface design using a free standing-type strain sensing structure and a skin sensor module comprising the same.

2. Description of the Related Art

After cleaning or in dry environment, the skin often feels tight. In this case, it is said that the skin is dry, and various attempts have been made to quantitatively measure dry skin.

To measure tightness feeling of skin, there were attempts to measure the elastic modulus of the skin, and the elastic modulus of the skin was measured by various techniques. Conventionally, the elastic modulus of the skin was measured using pressure-based suction, torsion, traction, nano-indentation, and ultrasound elastography, but the elastic modulus alone could not provide information associated with strain behavior of mechanical strain in the skin.

Furthermore, there were attempts to measure skin dryness by measuring the oil content or moisture content in the skin. To measure the skin moisture content, a method which measures the electrical properties such as impedance or capacitance using a device that is placed in contact with the skin surface was used. To measure the skin oil content, a method which uses a semi-transparent lipid absorbing tape or the principle of optical reflection was used.

Furthermore, there were attempts to measure skin dryness by measuring an amount of moisture evaporation from the epidermis. The attempts were made to measure an amount of moisture evaporation occurring at a cylinder region of 1 cm in diameter using a humidity sensor and a temperature sensor.

In addition, attempts have been made to measure skin dryness by measuring the skin type or mechanical properties. To measure elasticity, skin restoration over time after suction was measured. Through optical analysis, with a few tens of μm of resolution, texture, pores, wrinkles and dead skin cells were measured via visible light, and sebum, pores, troubles and acne were measured via ultraviolet light, and pigmentation, freckles and spots were measured using polarized light.

An ex-situ skin analysis method was vulnerable to many environmental factors affecting the skin such as humidity, temperature and fine dust, and it was difficult to measure the rate and degree at which skin dryness changes and to accurately describe the causes.

A wearable sensor device was used to measure the skin or health condition. The wearable sensor is a motion detection-based controller, and was used to measure or diagnose muscle motions or the heart rate and seizure in KR 10-1746492 B1. Furthermore, the sensor structure was adjusted to measure the maximum strain rates for each part.

The wearable sensor device as described in KR 10-1746492 B1 could measure only mechanical strain rates occurring in a large range (area $cm^2$), and focused on mechanical durability (maximum change rate), failing to sense very small changes (strain <1%). Furthermore, as measurements were carried out on the skin that was prevented from contacting the surrounding environment, it was the main object to measure muscle motions and the heart rate, and the device covering over the skin was difficult to monitor or measure skin changes caused by exposure to the external environment.

SUMMARY

The present disclosure is designed to solve the aforesaid problems, and therefore, the present disclosure is directed to providing a strain sensor unit for measuring skin strain and a skin sensor module comprising the same.

The present disclosure is further directed to providing a strain sensor unit with a wearable structure that is worn on the skin to measure skin strain based on physiological behavior of the skin while not affecting the skin condition by the worn sensor unit or module, and a skin sensor module comprising the same.

A strain sensor unit according to an embodiment of the present disclosure includes a substrate having a through-hole, and including a first electrode and a second electrode formed at one side and the other side of the through-hole on one surface of the substrate, a piezoelectric device drawn from the first electrode and extending inward the through-hole, and a piezoresistor drawn from the second electrode and extending inward the through-hole, wherein the piezoresistor overlaps with a whole or part of the piezoelectric device.

The piezoelectric device may be a piezoelectric semiconductor.

The piezoresistor may be a nanocrack-control based metal piezoresistive device.

An interfacial layer made of amorphous oxide semiconductor may be further formed on a contact surface between the piezoelectric device and the piezoresistor.

The substrate may have a plurality of air permeable holes of 50 to 150 μm.

A distance between the plurality of air permeable holes may be 50 to 150 μm.

The plurality of air permeable holes may comprise the through-hole.

The substrate may be made of a material including polydimethylsiloxane (PDMS).

A plurality of micro suction cups may be patterned on a surface opposite to one surface of the substrate to come into close contact with the skin.

A skin sensor module according to another embodiment of the present disclosure includes a substrate having a plurality of through-holes, and including a first electrode and a second electrode formed on one side and the other side of each through-hole on one surface of the substrate, a piezoelectric device drawn from each first electrode and extending inward the through-hole, and a piezoresistor drawn from each second electrode and extending inward the through-hole, wherein the piezoresistor overlaps with a whole or part of the piezoelectric device.

The piezoelectric device may be a piezoelectric semiconductor.

The piezoresistor may be a nanocrack-control based metal piezoresistive device.

An interfacial layer made of amorphous oxide semiconductor may be further formed on a contact surface between the piezoelectric device and the piezoresistor.

The substrate may have a plurality of air permeable holes of 50 to 150 μm.

A distance between the plurality of air permeable holes may be 50 to 150 μm.

All or some of the plurality of air permeable holes may comprise the plurality of through-holes.

The substrate may be made of a material including polydimethylsiloxane (PDMS).

A plurality of micro suction cups may be patterned on a surface opposite to one surface of the substrate to come into close contact with the skin.

The strain sensor unit may include the first electrode, the second electrode, and a strain sensing structure including the piezoelectric device and the piezoresistor, arranged with respect to one through-hole formed on the substrate, a plurality of strain sensor units may be formed on the substrate, and the plurality of strain sensor units may be arranged on the substrate in at least one array structure of a radial array structure, a linear array structure, a curved array structure, a crossed array structure, a circular array structure, a rectangular array structure, and a polygonal array structure.

A method for manufacturing a strain sensor unit according to another embodiment of the present disclosure includes stacking a substrate layer on a sacrificial layer, the substrate layer including a piezoresistor extending inward from one side of a through-hole of a substrate, attaching a piezoelectric device layer to a transfer structure and transferring onto the substrate layer, separating the transfer structure, and removing the sacrificial layer and an area of the piezoelectric device layer except an area corresponding to a piezoelectric device extending to the other side of the through-hole, covering a whole or part of the piezoresistor, and forming a first electrode and a second electrode at one side and the other side of the through-hole on one surface of the substrate, covering the piezoelectric device and the piezoresistor respectively.

The method for manufacturing a strain sensor unit may further include carrying out forming of a preset thickness of elastomer on a mold having micropillars, and separating the formed elastomer to form a substrate.

The attaching of a piezoelectric device layer to a transfer structure and transferring onto the substrate layer may include mounting a piezoelectric device layer on epitaxial graphene, mounting a stressor layer on the piezoelectric device layer, mounting a tape layer on the stressor layer, and separating the tape layer, the stressor layer and the piezoelectric device layer, and transferring onto the substrate layer.

A method for manufacturing a skin sensor module according to another embodiment of the present disclosure includes stacking a substrate layer on a sacrificial layer, the substrate layer including a piezoresistor extending inward from one side of each of a plurality of through-holes of a substrate, attaching a piezoelectric device layer to a transfer structure and transferring onto the substrate layer, separating the transfer structure, and removing the sacrificial layer and an area of the piezoelectric device layer except an area corresponding to a piezoelectric device extending to the other side of the through-hole, covering a whole or part of each piezoresistor, and forming a first electrode and a second electrode at one side and the other side of the plurality of through-holes on one surface of the substrate, covering the piezoelectric device and the piezoresistor respectively.

The method for manufacturing a skin sensor module may further include carrying out forming of a preset thickness of elastomer on a mold having a plurality of micropillars, and separating the formed elastomer to form a substrate.

The attaching of a piezoelectric device layer to a transfer structure and transferring onto the substrate layer may include mounting a piezoelectric device layer on epitaxial graphene, mounting a stressor layer on the piezoelectric device layer, mounting a tape layer on the stressor layer, and separating the tape layer, the stressor layer and the piezoelectric device layer, and transferring onto the substrate layer.

A skin strain sensor device according to another embodiment of the present disclosure includes the skin sensor module including a substrate having a plurality of through-holes and a test point to which stimulation to test is applied, and including a first electrode and a second electrode formed at one side and the other side of each through-hole on one surface of the substrate, a piezoelectric device drawn from each first electrode and extending inward the through-hole, and a piezoresistor drawn from each second electrode and extending inward the through-hole, wherein the piezoresistor overlaps with a whole or part of the piezoelectric device.

The test point may be an injection opening through which a material to test is injected, or an indentation point to which a preset magnitude or cycle of vibration is applied.

The plurality of through-holes may be arranged in a radial array structure with respect to the test point.

The skin strain sensor device may further include a retaining band connected to the skin sensor module and formed to encircle an arm or leg of a subject.

The skin sensor module may be further connected to a skin characteristic providing part, in which the skin sensor module measures a property of a wave according to pressure applied on the test point, and the skin characteristic providing part provides skin elasticity based on physical property of the tested skin induced from measured property of waves.

According to an embodiment of the present disclosure, there is provided a strain sensor unit for measuring skin strain and a skin sensor module comprising the same.

Furthermore, there is provided a strain sensor unit with a wearable structure that is worn on the skin to measure skin strain based on physiological behavior of the skin while not affecting the skin condition by the worn sensor unit or module, and a skin sensor module comprising the same.

DETAILED DESCRIPTION

Figure 1:
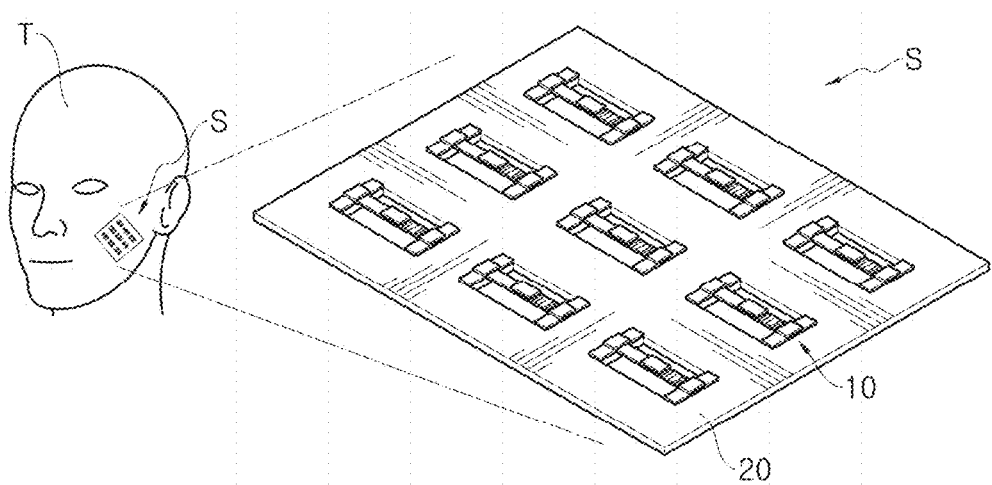
FIG. 1 is a diagram schematically showing a skin sensor module worn on a subject according to an embodiment of the present disclosure.

Various modifications may be made to the embodiments and the embodiments may have many embodiments, and a detail described will be provided by illustrating particular embodiments in the drawings. However, this is not intended to limit the scope of the particular embodiments, and should be understood as encompassing all modification, equivalents or alternatives included in the disclosed spirit and technical scope. In describing the embodiments, when details of relevant known technology are deemed to make the essence ambiguous, its detailed description is omitted herein.

In the embodiments, 'module' or 'unit' performs at least one function or operation, and may be implemented as either hardware or software or combination of hardware and software. Furthermore, except 'module' or 'unit' needed to be implemented as particular hardware, multiple 'module' or multiple 'unit' may be integrated into at least one module and implemented as at least one processor (not shown).

Hereinafter, the embodiments are described in detail with reference to the accompanying drawings, and in describing with reference to the accompanying drawings, identical or equivalent elements are given identical reference signs and the repeated description is omitted herein.

FIG. 1 is a diagram schematically showing a skin sensor module worn on a subject T according to an embodiment of the present disclosure.

The skin sensor module according to an embodiment of the present disclosure may be attached to the skin to measure mechanical changes in the skin. The skin sensor module S according to an embodiment includes a substrate 20 having a plurality of air permeable through-holes H and a plurality of strain sensor units 10 formed on the substrate.

The substrate 20 can be attached to the skin in close contact with the skin, and the strain sensor unit 10 is constructed as a free standing-type change sensing structure on the air permeable through-hole H. The strain sensor unit 10 may be attached to the though-hole H in free-standing form to sense skin changes by sensing changes in pressure applied to the change sensing structure with size changes of the through-hole H attached to the skin.

Figure 2:
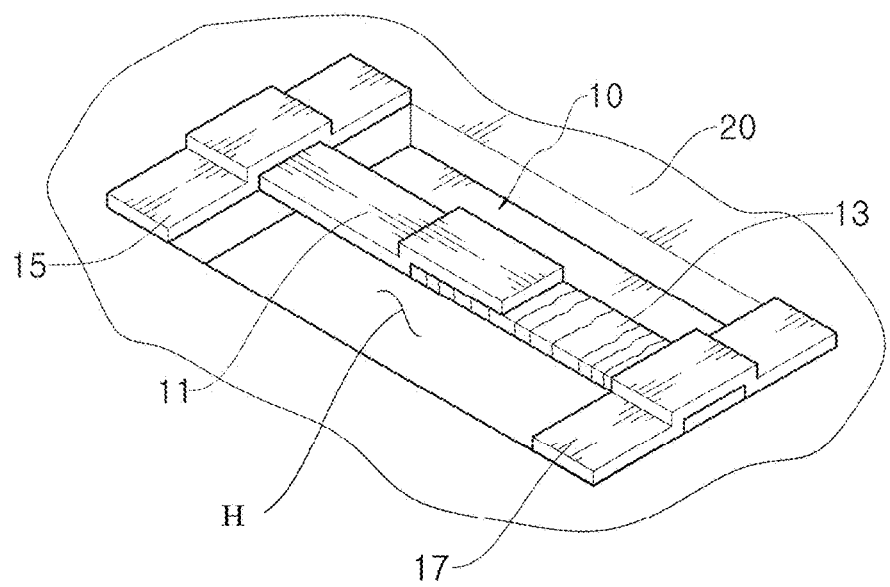
FIG. 2 is a diagram schematically showing a strain sensor unit according to an embodiment of the present disclosure.
Figure 3:
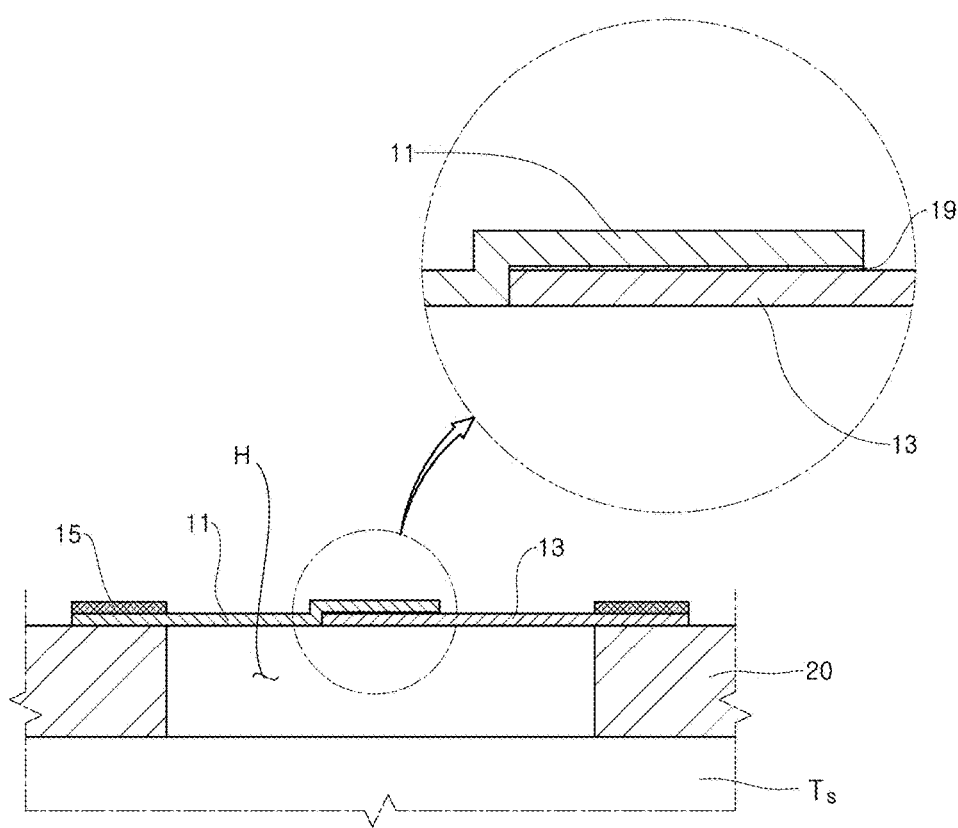
FIG. 3 is a cross-sectional view of a strain sensor unit according to an embodiment of the present disclosure.

FIG. 2 is a diagram schematically showing the strain sensor unit 10 according to an embodiment of the present disclosure, and FIG. 3 is a cross-sectional view of the strain sensor unit 10 according to an embodiment of the present disclosure.

Referring to FIGS. 2 and 3, the strain sensor unit 10 according to an embodiment of the present disclosure includes a substrate 20 having a through-hole H and including a first electrode 15 and a second electrode 17 formed at one side and the other side of the through-hole H on one surface of the substrate, a piezoelectric device 11 drawn from the first electrode 15 and extending inward the through-hole H, and a piezoresistor 13 drawn from the second electrode 17 and extending inward the through-hole H, wherein the piezoresistor 13 overlaps with the whole or part of the piezoelectric device 11.

According to an embodiment, the change sensing structure may include the piezoelectric device 11 and the piezoresistor 13. The change sensing structure extends across two sides of the through-hole H, and may be configured such that the pressure on the change sensing structure changes with changes in length. Accordingly, the change sensing structure may be formed to measure skin changes by sensing the pressure changes through the piezoelectric device and the piezoresistor.

The piezoelectric device 11 is a device that generates electrical signals in response to the mechanical pressure, and according to an embodiment, may be a piezoelectric semiconductor.

The piezoresistor 13 is a device of which resistance changes as nanometer-scale skin strain, and according to an embodiment, may be a nanocrack-control based metal piezoresistive device in which resistance of cracked metal changes by connection or disconnection of nanometer-scale cracks to measure skin strain on nanometer scale.

For example, the piezoresistor 13 may be a piezoresistive device with a silver (Ag) thin film on polyimide, having metal grains to induce resistance changes by connection or disconnection of cracks.

According to an embodiment, the strain sensor unit 10 may further include an interfacial layer 19 on contact surfaces of the piezoelectric device 11 and the piezoresistor 13. For example, the interfacial layer 19 may be a low-defective amorphous oxide semiconductor layer, and may be placed below the transfer-printed piezoelectric device 11.

Referring to the partial enlarged diagram of FIG. 3, the interfacial layer 19 formed on the contact layer between the piezoresistor 13 and the piezoelectric device 11 may comprise, for example, a Ga stoichiometry-controlled amorphous oxide interfacial layer, to form a low-defective Schottky barrier under a room temperature deposition process and improve sensitivity of the strain sensor.

Due to the amorphous structure, 1- and 2-dimensional defects are absent and a uniform contact can be formed. Further, Ga suppresses 0-dimensional defects such as oxygen deficiency, and induces ideal Schottky thermionic conduction. As a result, as the piezoelectric potential increases, the electrical resistance changes, i.e., sensitivity of the sensor increases.

Figure 4:
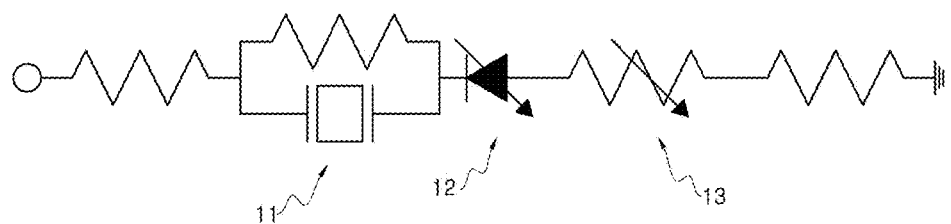
FIG. 4 is a circuit diagram of a strain sensor unit according to an embodiment of the present disclosure.

FIG. 4 is a circuit diagram of the strain sensor unit according to an embodiment of the present disclosure.

Referring to FIG. 4, the strain sensor unit according to an embodiment may have a structure in which the piezoelectric semiconductor type piezoelectric device 11 and the variable resistor type piezoresistor 13 are connected with a variable Schottky diode 12 between.

Figure 5A:
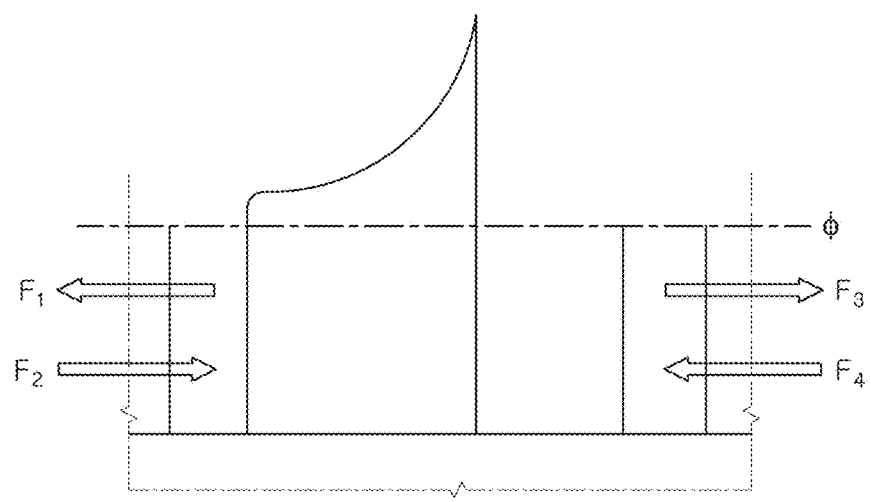
FIGS. 5A, 5B are graphs showing potential changes in the presence or absence of an interfacial layer in a strain sensor unit according to an embodiment of the present disclosure.
Figure 5B:
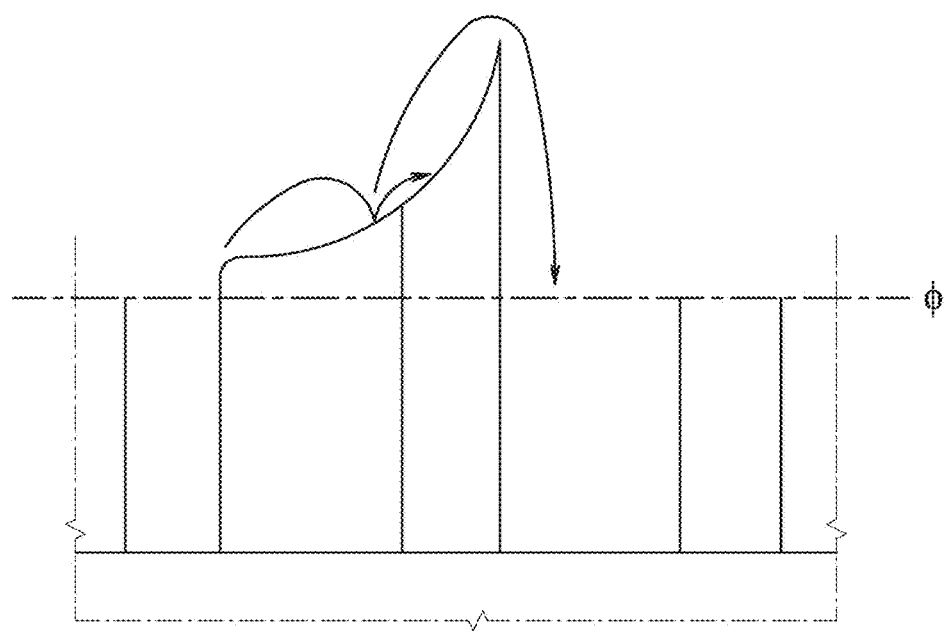

FIGS. 5A, 5B are graphs showing energy band diagram in the presence or absence of the interfacial layer in the strain sensor unit according to an embodiment of the present disclosure.

FIG. 5A is an energy band diagram of the strain sensor unit of an embodiment in which the piezoelectric device 11 and the piezoresistor 13 are connected to each other, and FIG. 5B is an energy band diagram of an embodiment further including the interfacial layer 19.

Referring to FIG. 5A, in case that forces of $F_1$ and $F_3$ are applied and a tensile force is applied, the barrier height increases, and the resistance of the piezoresistor 13 increases.

Furthermore, in case that forces of $F_2$ and $F_4$ are applied and the pressure is applied, the barrier height reduces, and the resistance of the piezoresistor 13 reduces.

That is, in case that tightness occurs in the skin to which the strain sensor unit is attached ($F_1$, $F_3$), or the skin becomes loose ($F_2$, $F_4$), the Schottky barrier may be adjusted based on Fermi energy level to sense tightness and looseness of skin.

Accordingly, sensitivity of the strain sensor unit can be greatly enhanced through a series of interconnections of the piezoelectric device 11 and the piezoresistor 13. As a result, the strain sensor unit capable of sensing nanometer-scale skin changes can be provided.

Referring to FIG. 5B, it can be seen that the addition of the amorphous oxide interfacial layer 19 eliminates 1- and 2-dimensional defects at the interface, thereby suppressing tunneling conduction that occurs irrespective of the Schottky barrier height and creating ideal Schottky thermionic conduction.

Figure 6:
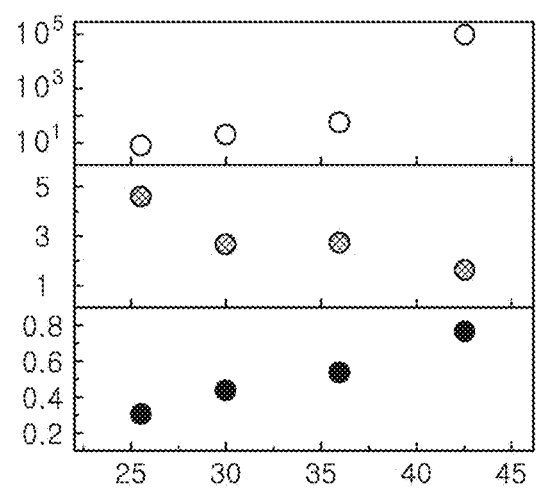
FIG. 6 is a graph showing changes in electrical properties of an interfacial layer.

FIG. 6 is a graph showing changes in electrical properties of the amorphous oxide interfacial layer. It can be seen that Schottky thermionic conduction parameter values change by adjusting stoichiometry of amorphous oxide, and optimal stoichiometry is set to ensure ideal Schottky thermionic conduction properties.

A skin sensor module according to another embodiment of the present disclosure includes a plurality of strain sensor units to sense physical changes of the skin at a skin area within a preset range.

The skin sensor module according to an embodiment includes a substrate having a plurality of through-holes and including a first electrode and a second electrode formed at one side and the other side of each through-hole on one surface of the substrate, a piezoelectric device drawn from each first electrode and extending inward the through-hole, and a piezoresistor drawn from each second electrode and extending inward the through-hole, wherein the piezoresistor overlaps with the whole or part of the piezoelectric device.

In other words, the strain sensor unit in the skin sensor module may be configured as one unit including the first electrode, the second electrode, and the strain sensing structure composed of the piezoelectric device and the piezoresistor, arranged with respect to one through-hole on the substrate, to sense skin strain at one point.

The plurality of strain sensor units formed on the substrate may be arranged on the substrate in at least one array structure of a radial array structure, a linear array structure, a curved array structure, a crossed array structure, a circular array structure, a rectangular array structure, and a polygonal array structure.

In the specification, the description of the strain sensor unit may be applied to the skin sensor module, or vice versa. The repeated description is omitted herein.

Hereinafter, methods for manufacturing the strain sensor unit and the skin sensor module comprising the same will be described in more detail.

The following description is made based on a method for manufacturing a skin sensor module including a plurality of strain sensor units, but is not necessarily limited thereto, and it may be also applied to a method for manufacturing a strain sensor unit.

Figure 7:
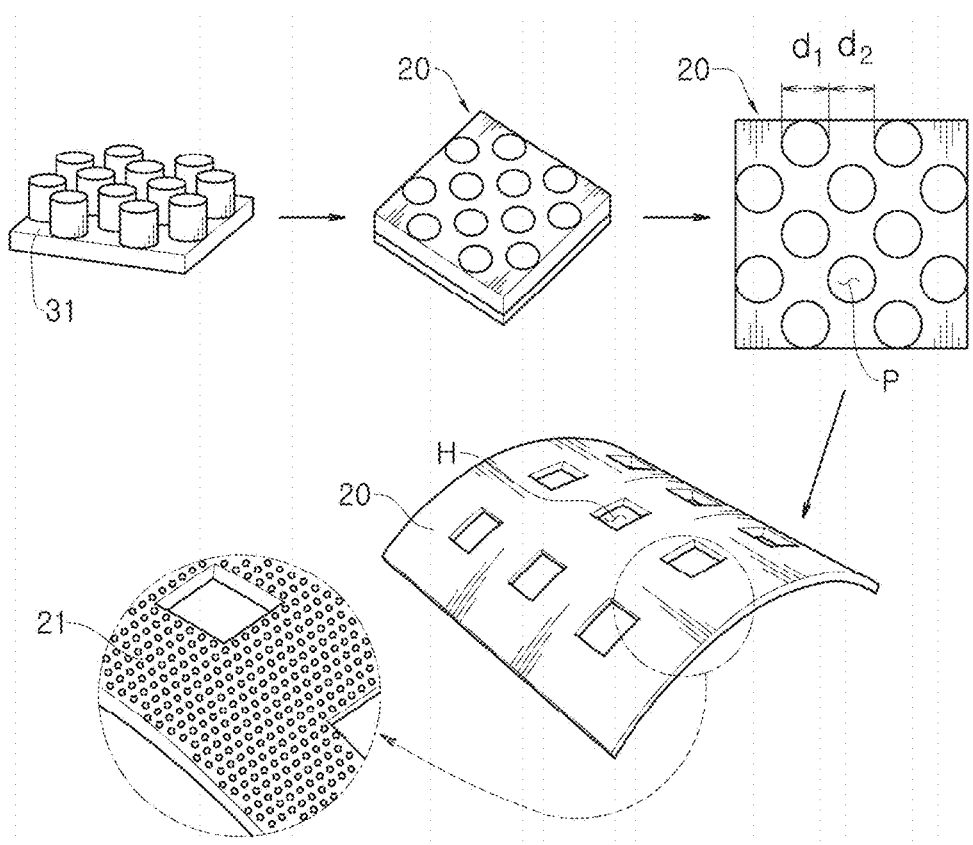
FIG. 7 is a diagram schematically showing a process for manufacturing a flexible adhesive substrate according to an embodiment of the present disclosure.

FIG. 7 is a diagram schematically showing a process for manufacturing a flexible adhesive substrate according to an embodiment of the present disclosure.

The pore size in normal skin is approximately 100 μm, and the distance between adjacent pores is approximately 100 μm. The skin has 2 million to 4 million pores in total, and pores are distributed over the skin with the density of approximately 11.4/cm². Watery discharge from the skin by transpiration of the skin is approximately 2 to 5 μm in diameter, and includes 99% of water ($H_2O$) as a main component, and Na, Cl, K, N, etc. Furthermore, approximately 700 mL of water is discharged from the skin every day.

The flexible adhesive substrate 20 according to an embodiment of the present disclosure may have a plurality of air permeable holes P having the diameter $d_1$ of approximately 100 μm (50 μm to 150 μm) and the distance $d_2$ of approximately 100 μm (50 μm to 150 μm) therebetween. In case that the diameter $d_1$ and the distance $d_2$ are less than 50 μm, the flexible adhesive substrate is placed in close contact with the skin, hindering the moisture discharge from the skin, and in case that the diameter $d_1$ and the distance $d_2$ exceed 150 μm, it is difficult to ensure a desired level of durability.

Because the plurality of air permeable holes is formed in the flexible adhesive substrate, the flexible adhesive substrate ensures breathability. That is, it is possible to accurately measure skin dryness occurring due to the exposure to real external environment while minimizing the influence of the flexible adhesive substrate on transpiration of the skin.

According to an embodiment, the air permeable holes P are shown as having a circular shape, but are not necessarily limited thereto, and the air permeable holes may have various shapes including quadrilateral or polygonal shapes, or etc.

According to an embodiment, the air permeable hole P may be used as the though-hole H of the strain sensor unit. Without a separate through-hole H, the strain sensing structure may be placed on the air permeable hole P to sense skin changes. However, the present disclosure is not necessarily limited thereto, and the air permeable hole P and the through-hole H may be separately manufactured and used.

Referring to the first diagram in the flowchart of FIG. 7, a mold 31 having a plurality of micropillars is prepared first. The micropillars formed in the mold 31 are formed with the size and shape corresponding to the through-holes H.

Referring to the second diagram in FIG. 7, a material that constitutes a substrate 20 may be formed on the mold 31. For example, forming of a preset thickness of elastomer on the mold 31 may be performed. According to an embodiment, the elastomer is a material including polydimethylsiloxane (PDMS) that can be tightly attached to the skin while minimizing the influence on the skin and may constitute the substrate 20.

Subsequently, referring to the third diagram in FIG. 7, the substrate 20 is separated from the mold 31, to form the substrate 20 having a plurality of air permeable holes P.

Referring to the fourth diagram in FIG. 7, the substrate 20 according to another embodiment of the present disclosure includes a plurality of quadrilateral air permeable holes P, and the air permeable holes P may comprise the through-hole H for the strain sensor unit. Accordingly, the strain sensor units may be mounted on each through-hole H to form the skin sensor module.

Furthermore, a plurality of micro suction cups 21 may be patterned on the lower surface of the substrate 20. Accordingly, the skin sensor module capable of measuring skin strain in closer contact with the skin can be provided.

FIGS. 8A, 8B, 8C, 8D are diagrams schematically a process for manufacturing the skin sensor module according to an embodiment of the present disclosure. The manufacturing process for mounting the strain sensor unit on the substrate 20 formed as described above will be described with reference to FIGS. 8A, 8B, 8C, 8D.

Figure 8A:
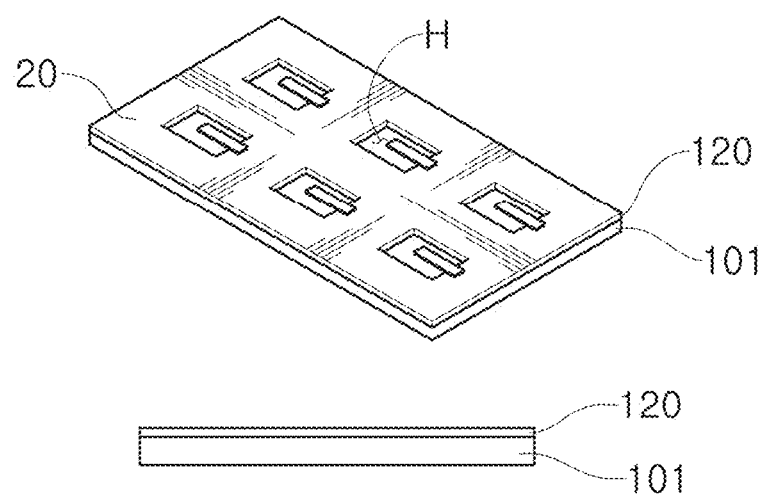
FIGS. 8A, 8B, 8C, 8D are diagrams schematically a process for manufacturing a skin sensor module according to an embodiment of the present disclosure.

Referring to FIG. 8A, the substrate 20 is stacked on a sacrificial layer 101, and piezoresistors 13 extending inward from one side of through-holes H of the substrate is stacked to form a substrate layer 120. The present disclosure is not necessarily limited thereto, and the substrate layer 120 including the piezoresistors 13 extending inward from one side of the substrate may be stacked on the sacrificial layer 101.

Figure 8B:
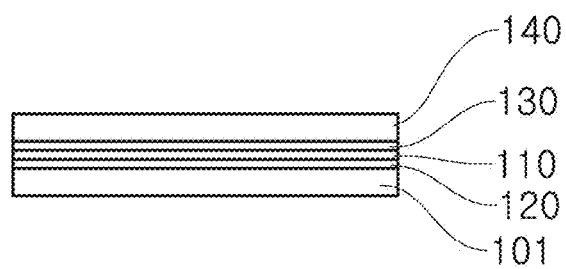

Referring to FIG. 8B, a piezoelectric device 110 may be attached to a transfer structure, and may be then transferred onto the substrate layer 120.

According to an embodiment, the piezoelectric device layer 110 may be mounted on epitaxial graphene (for example, SiC layer), then, a stressor layer 130 (for example, Ni layer) may be formed on the piezoelectric device layer 110, and a tape layer 140 may be formed thereon. Accordingly, to transfer the piezoelectric device layer 110, the transfer structure of the stressor layer 130 and the tape layer 140 may be formed thereon.

That is, the piezoelectric devices 110 such as high-performance, single crystal piezoelectric semiconductors (AlN, GaN) may be transferred onto the substrate layer 120 within the range of approximately 90° C. using Graphene-Based Layer Transfer printing (GBLT).

According to an embodiment of the present disclosure, the sensing performance of the piezoelectric strain sensor can be enhanced by reduction in defects such as dislocation and grain boundary and modulation of desirable crystal orientation.

Figure 8C:
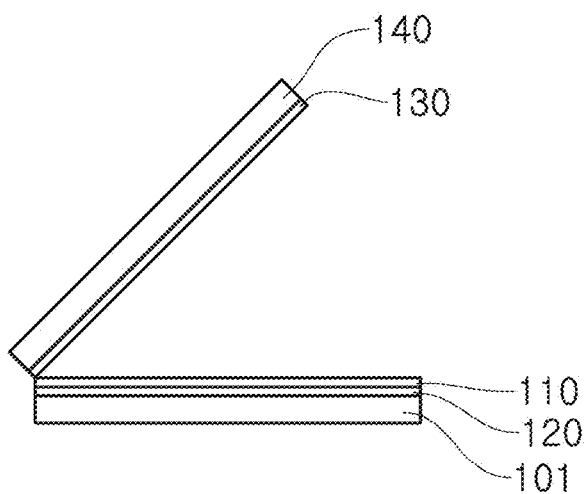
Figure 8D:
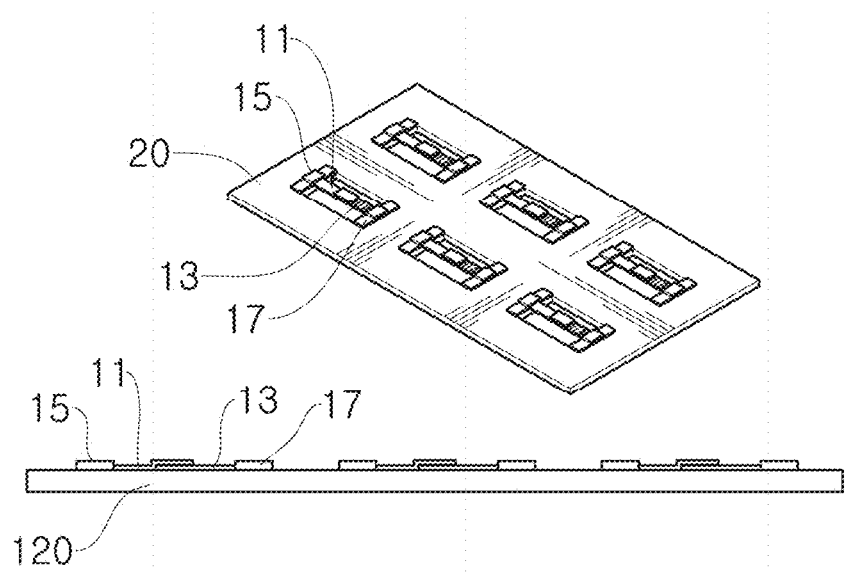

Referring to FIG. 8C, the transfer structure of the stressor layer 130 and the tape layer 140 may be taken, leaving a stack of the piezoelectric device layer 110, the substrate layer 120 having the piezoresistors 13, and the sacrificial layer 110 stacked in a sequential order.

Furthermore, the sacrificial layer 101 and the remaining part not corresponding to the piezoelectric device 11 in the piezoelectric device layer 110 may be removed through a process such as etching. Furthermore, a first electrode 15 and a second electrode 17 may be printed through a process such as printing, to form a skin sensor module having a plurality of strain sensor units.

FIG. 9 is a diagram schematically showing a process for measuring skin changes by the strain sensor unit according to an embodiment of the present disclosure.

Referring to FIG. 9, the strain sensor unit 10 according to an embodiment may be detachably attached to the skin Ts, Td. The skin includes the cornified layer Ts and the dermal layer Td. The strain sensor unit 10 is placed in close contact with the surface of the cornified layer Ts to measure changes of the through-hole H.

Because the substrate 20 according to an embodiment of the present disclosure includes micro-sized holes, the substrate 20 does not affect the physiological activities of the skin and impede skin dryness, and thus can provide breathability of the skin.

Because the change sensing structure (the piezoelectric device 11 and the piezoresistor 13) hangs on the hole providing breathability of the substrate in free standing type, the change sensing structure can effectively bend according to skin strain induced by mechanical stress.

Particularly, mechanical changes of the cornified layer in the skin may be analyzed based on the thin film mechanism. The skin is composed of the cornified layer up to approximately 20 μm, and the epidermal layer and the dermal layer up to approximately 2 mm. Accordingly, in case that the dermal layer is seen as a substrate, the cornified layer has a thin film structure at a ratio of approximately 1/100 to the dermal layer. Accordingly, in case that skin dryness occurs, volume contraction of the cornified layer of relatively thin film type is induced.

Furthermore, in case that dryness occurs, initially, the cornified layer reduces in water content and is contracted, while the dermal layer becomes relatively less dry, and thus, the dermal layer attracts the cornified layer and tensile stress occurs. However, in case that dryness continues, the elastic modulus of the cornified layer increases, and crack occurs in the cornified layer Ts, leading to a loss of protection function. Furthermore, in case that crack occurs, the tensile stress reduces and the skin gets loose.

Accordingly, continuous monitoring of mechanical behavior of the cornified layer can play a very important role in identifying skin health.

In the specification, a skin change rate may be defined by the following [Equation 1] using the initial length $L_0$ of the skin at a preset region and the length $L_t$ after the time t:

Change rate (%)=length change $(L_t-L_0)$/initial length $(L_0)\times 100$     [Equation 1]

That is, a skin change rate can be provided as a quantitative value by calculating a length change of the change sensing structure (the piezoelectric device 11 and the piezoresistor 13).

Figure 9A:
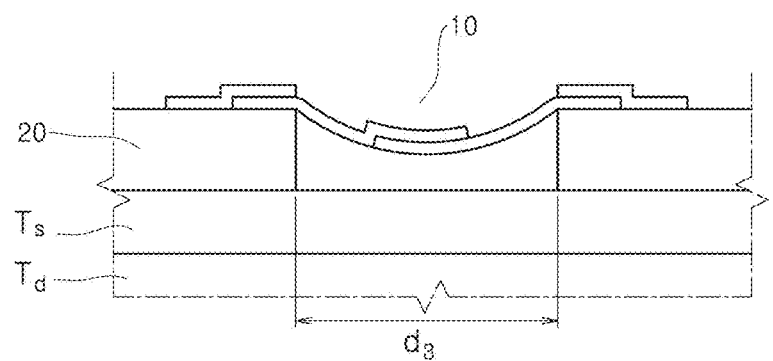
FIGS. 9A, 9B, 9C are diagrams schematically showing a process for measuring skin changes by a strain sensor unit according to an embodiment of the present disclosure.

Referring to the start step of FIG. 9A, the change sensing structure (the piezoelectric device 11 and the piezoresistor 13) when not subjected to pressure may have the length of d3.

Figure 9B:
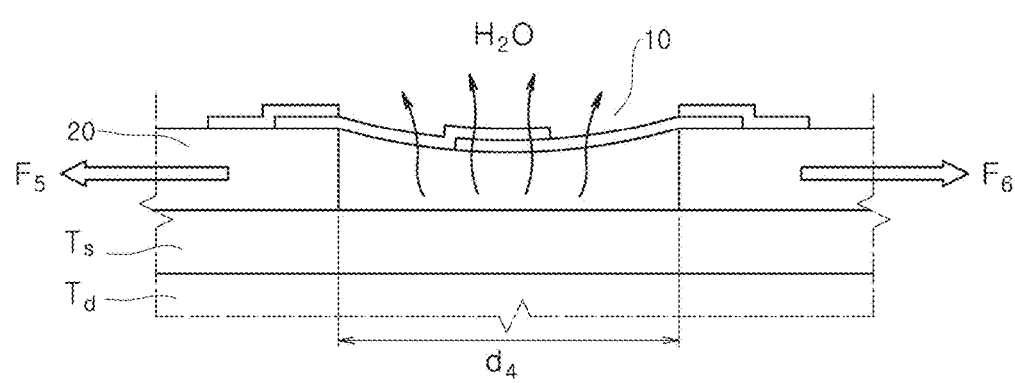

Referring to the initial step of FIG. 9B, when materials including moisture are discharged from the skin over time and the cornified layer becomes dry first, tensile stress $F_5$, $F_6$ occurs in the cornified layer. In this case, the change sensing structure (the piezoelectric device 11 and the piezoresistor 13) may have the length of d4, and d4 has a longer length than d3. Furthermore, in this case, it may be determined that skin tightness of the subject occurred.

Figure 9C:
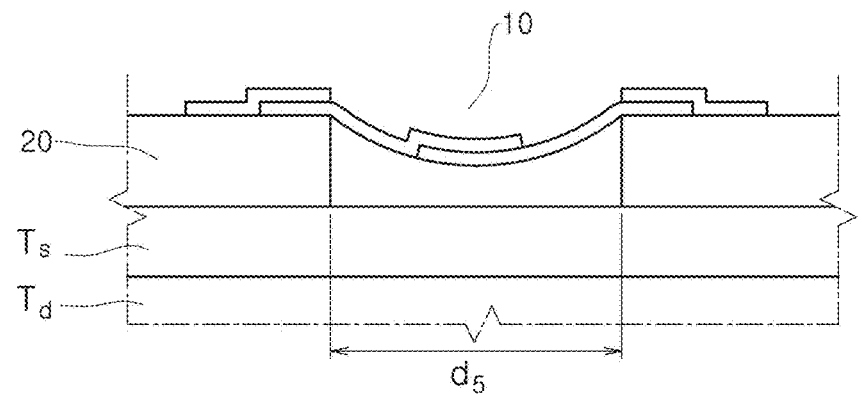

Referring to the last step of FIG. 9C, when dryness continues, cracks C occur in the cornified layer, and the tensile stress applied to the change sensing structure (the piezoelectric device 11 and the piezoresistor 13) reduces, and in this case, the change sensing structure may have the length of d5. d5 has a shorter length than d4.

In this way, skin changes may be measured based on the pressure applied to the change sensing structure (the piezoelectric device 11 and the piezoresistor 13) or the length of the change sensing structure.

Figure 10:
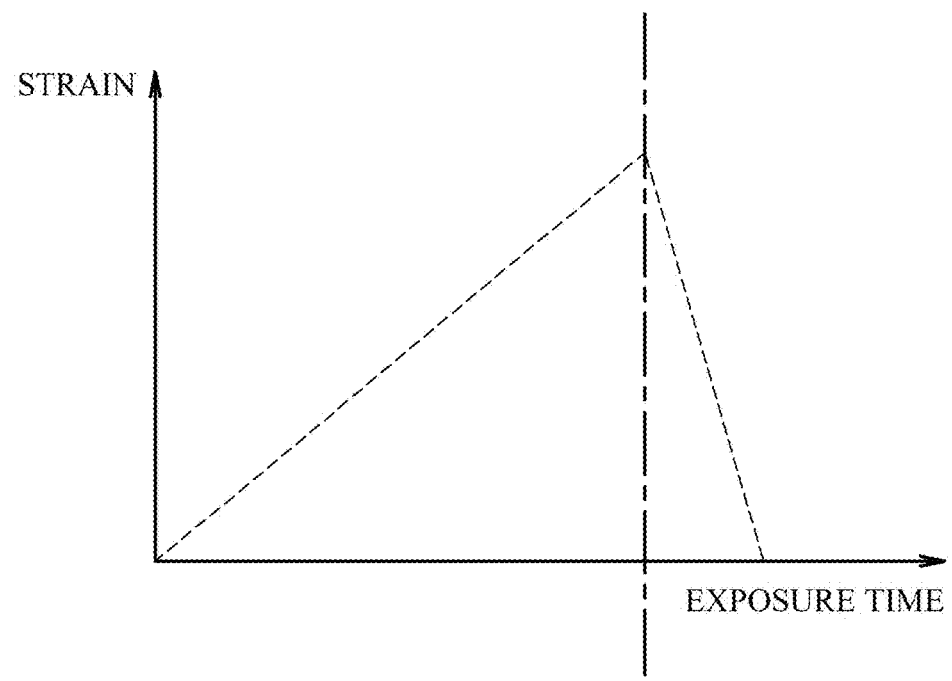
FIG. 10 is a graph showing skin changes over time, measured by a strain sensor module according to an embodiment of the present disclosure.

FIG. 10 is a graph showing skin strain rate over time, measured by the strain sensor module according to an embodiment of the present disclosure.

The start step of FIG. 9A corresponds to exposure start time in the graph of FIG. 10, and at the initial step of FIG. 9B, as the cornified layer gets dry, the tensile stress increases and the skin strain continuously increases.

Then, at the last step of FIG. 9C, as crack is formed in the cornified layer, the tensile stress reduces again and the strain returns to the condition equal or similar to the initial condition.

Figure 11:
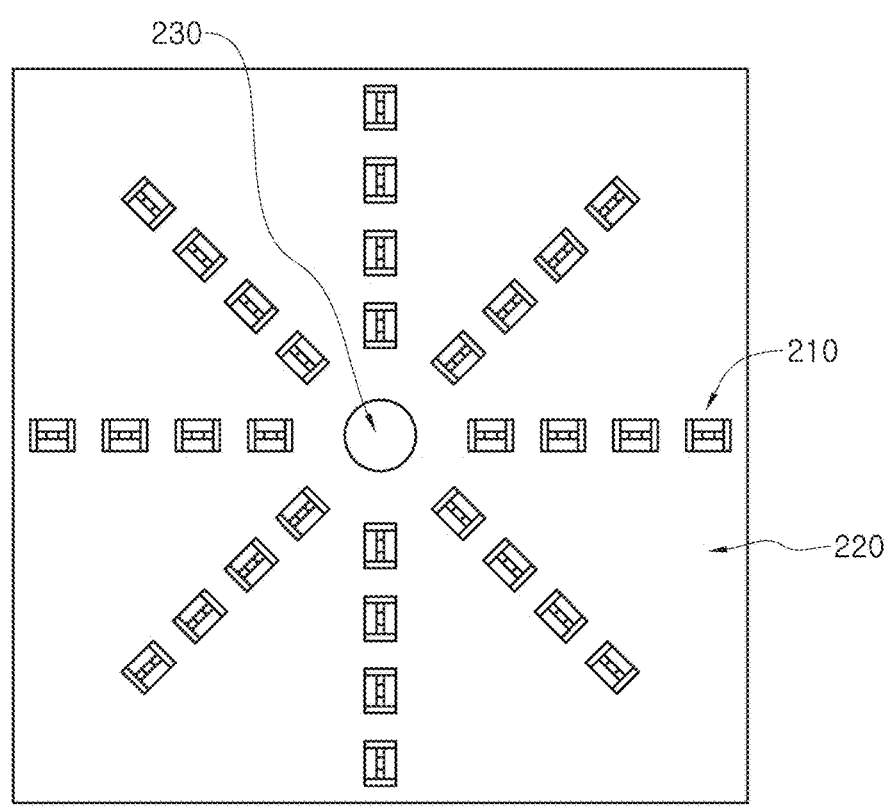
FIG. 11 is a diagram schematically showing a skin sensor module according to another embodiment of the present disclosure.

FIG. 11 is a diagram schematically showing a skin sensor module according to another embodiment of the present disclosure.

Diffusion dynamics of percutaneous drug and cosmetic delivery were examined by imaging the cross section of the skin using fluorescence photomicroscopes, gradual tape stripping, or in-vitro testing using a skin permission device (diffusion cells). All of these methods may cause damage to the skin, and have a very tedious testing process and are very difficult to derive diffusion of drugs or cosmetics due to discontinuity in results.

Referring to FIG. 11, a skin strain sensor device according to an embodiment of the present disclosure includes a skin sensor module, and the skin sensor module is composed of a substrate 220, and a test point formed on the substrate 220 to which stimulation to test is applied and a plurality of strain sensor units 210 arranged with respect to the test point.

The test point may be an injection opening 230 through which a material to test for a diffusion test is injected, or an indentation point at which a preset magnitude of vibration is applied to the skin for an indentation test. Furthermore, the plurality of strain sensor units 210 may be arranged in radial array structure with respect to the test point.

Specifically, according to an embodiment, the skin sensor module includes the substrate 220, and the injection opening 230 formed on the substrate 220 and the plurality of strain sensor units 210 arranged radially, i.e., in radial array structure, with respect to the injection opening 230.

The strain sensor units 210 are arranged in 360 degree radial array, and the skin strain sensor device may be used to measure diffusivity by injecting a material to test (for example, drugs or cosmetics) through the injection opening 230.

According to another embodiment, the skin sensor module may include the substrate 220, and the indentation point (not shown) formed on the substrate 220 and the plurality of strain sensor units 210 arranged radially, i.e., in 360 degree radial array structure, with respect to the indentation point.

A preset magnitude or cycle of vibration may be generated on the skin with respect to the indentation point. Furthermore, the plurality of strain sensor units 210 arranged with respect to the indentation point may measure elasticity and viscoelasticity of the epidermal layer and/or the dermal layer of the subject or all these features by analyzing the velocity at which the vibration is transmitted to the skin and/or waveform of the vibration.

In FIG. 11, the indentation point may be disposed at a location corresponding to the injection opening 230, and may be placed in the shape of an opening or a mark representing an indentation reference point to indicate a reference point to which a predetermined magnitude of vibration pressure is applied. The indentation point is not necessarily limited thereto, and may have various shapes to indicate an indentation reference point.

According to an embodiment of the present disclosure, diffusivity of drugs or cosmetics can be measured in a simple, non-surgical, in-vivo manner by using the skin sensor module. The diffusion in the lateral direction from the injection opening 230 and the diffusion length may be measured through skin strain measurements using the strain sensor units 210 radially arranged. Furthermore, Arrhenius activation energy of diffusion can be derived through measurements of temperature dependency of diffusion.

Figure 12:
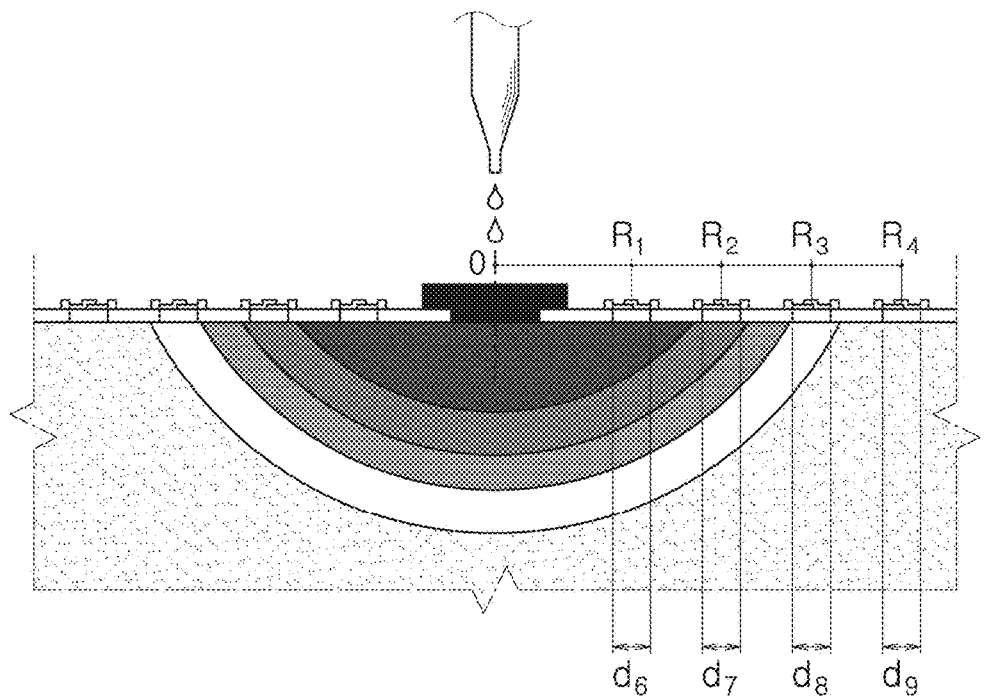
FIG. 12 is a cross-sectional view of the skin sensor module of FIG. 11.

FIG. 12 is a cross-sectional view of the skin sensor module of FIG. 11. Referring to FIG. 12, the diffusion length and the diffusion rate may be measured using the skin sensor module according to an embodiment of the present disclosure as below.

Specifically, the skin sensor module is mounted on the skin. Subsequently, a drug or cosmetic to test is injected through the injection opening 230.

The plurality of strain sensor units may be each arranged at the position $R_1$, position $R_2$, position $R_3$, and position $R_4$ from the injection opening 230. Furthermore, the diffusion length and the diffusion rate may be measured through calculation of the lengths d6, d7, d8, and d9 of the change sensing structures of each sensor.

From the point in time at which the drug or cosmetic is injected through the injection opening 230, the time at which changes are sensed by the strain sensor units at each position and locations of the corresponding positions are measured. Subsequently, the diffusion distance and the diffusion rate may be calculated based on the location of position and the time at which strain is sensed from the opening.

Referring to FIG. 12, a change rate of the length d6 at the position $R_1$ placed at the center from the injection opening 230 is greatest, change rates of the lengths d7 and d8 at the positions $R_2$ and $R_3$ in a sequential order gradually reduce, and strain caused by the cosmetic ingredients may not be sensed by the strain sensor units subsequent to the position $R_4$. In this case, it may be determined that the cosmetic ingredients are diffused approximately to the position $R_3$.

In the case of diffusion of drugs or cosmetics in skin, it is difficult to measure the diffusion rate in the depthwise direction and its effect without causing damage to the skin. Accordingly, the diffusion rate and effect may be calculated by measuring the diffusion rate and effect in the lateral direction (left/right direction) to measure the diffusion rate and effect while not damaging the skin.

Figure 13:
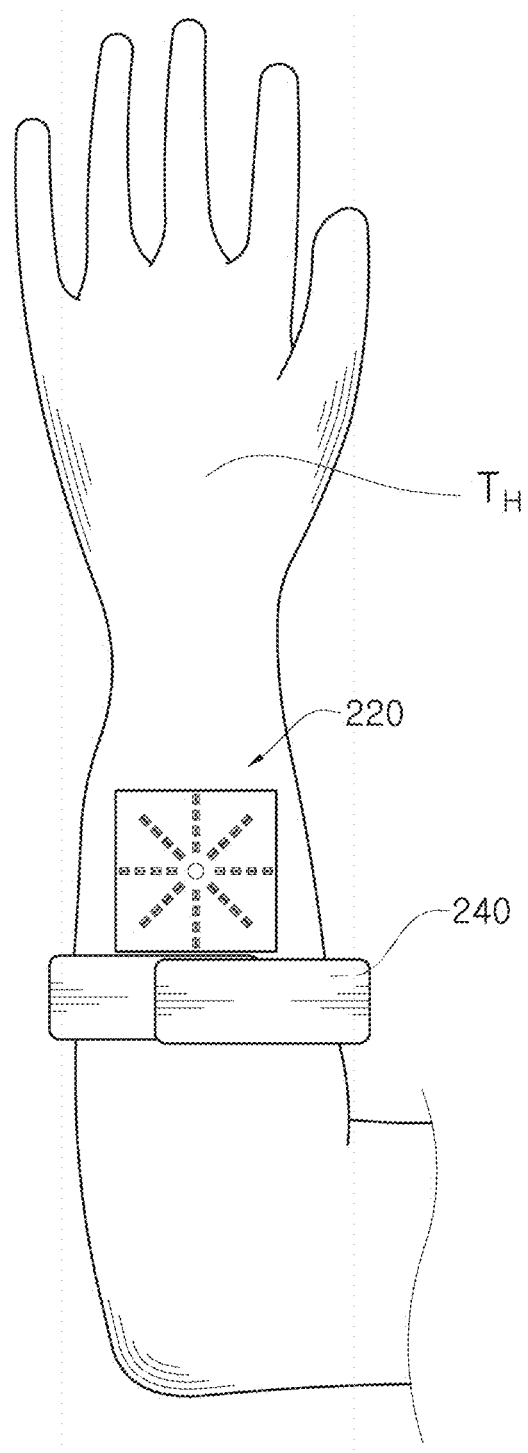
FIG. 13 is a diagram showing a skin strain sensor device according to an embodiment of the present disclosure.

FIG. 13 is a diagram showing the skin strain sensor device according to an embodiment.

The skin strain sensor device according to an embodiment of the present disclosure includes a skin sensor module 220 and a retaining band 240 fixed thereto, and may be mounted on the arm $T_H$ of the subject to measure skin diffusion. That is, in-vivo testing is possible without damaging the skin. Furthermore, the skin sensor module capable of observing skin changes by monitoring skin changes in real time can be provided.

According to the present disclosure, there is provided the strain sensor unit in which micro-sized holes are formed on the substrate, ensuring high breathability or air permeability. Accordingly, there is provided the strain sensor unit that can measure mechanical strain of the skin in real time while not affecting physiological activities (such as, for example, dryness) of the skin, or the skin sensor module comprising the same.

The change sensing structure of the strain sensor unit of the present disclosure is a free standing-type structure such that it hangs on the hole of the substrate, and is efficiently bent by mechanical stress inducing skin strain to measure skin strain.

Furthermore, because piezoelectric semiconductors are single crystal having low defect density, the outstanding sensitivity performance is provided. Furthermore, the interfacial defect density at Schottky contact is also reduced by the amorphous oxide interfacial layer.

The percutaneous diffusion characteristics of drugs and cosmetics are calculated by measuring skin strain from the injection opening using the skin sensor module, thereby conducting a non-surgical, in-vivo, and real-time test of diffusion characteristics.

Furthermore, the strain sensor unit, the skin sensor module comprising the same, and the skin strain sensor device according to various embodiments of the present disclosure can be used to measure skin tightness but also to measure elasticity of the skin.

According to one embodiment, the skin sensor module 220 may be further connected to a skin characteristic providing part, thereby can be used to providing various skin characteristics.

When skin strain is induced by applying physical pressure to the skin, skin elasticity differs depending on gender, age and skin condition, making a difference in degree of skin strain. That is, when the pressure is applied to the center of the array of the sensors, a degree of deformation of the skin can be measured according to differences in properties of waves (such as, wavelength, wave shape, cycle, propagation speed, etc) varied from skin properties, and physical properties of the skin can be derived therefrom. After then, a difference in skin elasticity can be measured based on the physical properties of the skin.

For example, the skin sensor module measures a property of a wave according to pressure applied on the test point, and the skin characteristic providing part provides skin elasticity based on physical property of the tested skin induced from the measured property of the wave.

DETAILED DESCRIPTION OF MAIN ELEMENTS

10: Strain sensor unit
11: Piezoelectric device
13: Piezoresistor
15: First electrode
17: Second electrode
19: Interfacial layer
20: Substrate

What is claimed is:

1. A strain sensor unit comprising:
a substrate having a through-hole;
a piezoelectric device located at one side of the through-hole on the substrate, and extending toward another side of the through-hole;
a piezoresistor located at another side of the through-hole on the substrate, and extending toward one side of the through-hole;
a first electrode located on the piezoelectric device; and
a second electrode located on the piezoresistor,
wherein the piezoresistor overlaps with a whole or part of the piezoelectric device, and
wherein the piezoresistor is a nanocrack-control based metal piezoresistive device.

2. The strain sensor unit according to claim 1, wherein the piezoelectric device is a piezoelectric semiconductor.

3. The strain sensor unit according to claim 1, wherein an interfacial layer made of amorphous oxide semiconductor is further formed on a contact surface between the piezoelectric device and the piezoresistor.

4. The strain sensor unit according to claim 1, wherein the substrate has a plurality of air permeable holes having the diameter of 50 to 150 μm.

5. The strain sensor unit according to claim 4, wherein a distance between the plurality of air permeable holes is 50 to 150 μm.

6. The strain sensor unit according to claim 4, wherein the plurality of air permeable holes comprises the through-hole.

7. The strain sensor unit according to claim 1, wherein the substrate is made of a material including polydimethylsiloxane (PDMS).

8. The strain sensor unit according to claim 1, wherein a plurality of micro suction cups is patterned on a surface opposite to one surface of the substrate to be attached to the skin.

* * * * *

UNITED STATES PATENT AND TRADEMARK OFFICE
CERTIFICATE OF CORRECTION

PATENT NO. : 10,952,642 B2
APPLICATION NO. : 15/808416
DATED : March 23, 2021
INVENTOR(S) : Han et al.

Page 1 of 1

It is certified that error appears in the above-identified patent and that said Letters Patent is hereby corrected as shown below:

On the Title Page

Item (72), "Han-Wool Yeon" should read: Han-Wool Yeun.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*